US010416058B2

United States Patent
Buzek et al.

(10) Patent No.: US 10,416,058 B2
(45) Date of Patent: Sep. 17, 2019

(54) VARIABLE ECCENTRIC CAM RHEOMETER SYSTEM

(71) Applicant: Alpha Technologies Services LLC, Akron, OH (US)

(72) Inventors: Keith Buzek, Akron, OH (US); Matthew S. McMaster, Wadsworth, OH (US); Michael R. Stoller, Orrville, OH (US)

(73) Assignee: ALPHA TECHNOLOGIES SERVICES LLC, Akron, OH (US)

( * ) Notice: Subject to any disclaimer, the term of this patent is extended or adjusted under 35 U.S.C. 154(b) by 217 days.

(21) Appl. No.: 15/519,222

(22) PCT Filed: Oct. 8, 2015

(86) PCT No.: PCT/US2015/054660
§ 371 (c)(1),
(2) Date: Apr. 14, 2017

(87) PCT Pub. No.: WO2016/060927
PCT Pub. Date: Apr. 21, 2016

(65) Prior Publication Data
US 2017/0241885 A1   Aug. 24, 2017

Related U.S. Application Data

(60) Provisional application No. 62/063,611, filed on Oct. 14, 2014.

(51) Int. Cl.
*G01N 11/16* (2006.01)
*G01N 3/26* (2006.01)
*G01N 3/34* (2006.01)

(52) U.S. Cl.
CPC ............ *G01N 11/162* (2013.01); *G01N 3/26* (2013.01); *G01N 3/34* (2013.01); *G01N 11/165* (2013.01);
(Continued)

(58) Field of Classification Search
CPC .......... G01N 11/162; G01N 3/34; G01N 3/26; G01N 11/165; G01N 2203/0266;
(Continued)

(56) References Cited

U.S. PATENT DOCUMENTS 2,919,925 A * 1/1960 Snyder ...................... E21B 3/04
279/123
3,247,598 A 4/1966 Wilkes
(Continued)

FOREIGN PATENT DOCUMENTS

JP    2010-261760 A    11/2010

OTHER PUBLICATIONS

Crosman 22XX 88g AirSource Adapter—Part 2 (Airgun Blog). (Year: 2011).*
(Continued)

*Primary Examiner* — Randy W Gibson
*Assistant Examiner* — Gedeon M Kidanu
(74) *Attorney, Agent, or Firm* — Shumaker, Loop & Kendrick, LLP; James D. Miller

(57) ABSTRACT

The present application relates generally to moving die rheometers, and more particularly to moving die rheometers that employ a variable eccentric cam. In one aspect, the eccentricity produced by the cam may be adjusted using shims of different thickness to alter the position of the post on the cam.

9 Claims, 6 Drawing Sheets

(52) U.S. Cl.
CPC ............... *G01N 2203/0007* (2013.01); *G01N 2203/0021* (2013.01); *G01N 2203/0037* (2013.01); *G01N 2203/0266* (2013.01)

(58) Field of Classification Search
CPC ... G01N 2203/0037; G01N 2203/0021; G01N 2203/0007
See application file for complete search history.

(56) References Cited

U.S. PATENT DOCUMENTS

| | | | |
|---|---|---|---|
| 3,494,172 A | 2/1970 | Juve et al. | |
| 3,681,980 A | 8/1972 | Decker | |
| 4,343,190 A * | 8/1982 | Danko | G01N 11/165 73/54.39 |
| 4,880,218 A | 11/1989 | Greene | |
| 5,481,903 A * | 1/1996 | King | G01N 11/165 73/54.28 |
| 6,681,617 B1 * | 1/2004 | Putman | G01N 11/142 73/54.27 |
| 2003/0183016 A1 * | 10/2003 | Prescott | G01N 11/165 73/841 |
| 2014/0260558 A1 * | 9/2014 | McMaster | G01N 11/165 73/54.01 |

OTHER PUBLICATIONS

International Search Report and Written Opinion for International Application No. PCT/US2015/054660, dated Jan. 4, 2016.
International Preliminary Report on Patentability for International Application No. PCT/US2015/054660, dated Apr. 27, 2017.
[No Author Listed] Crosman 22XX 88g AirSource Adapter—Part 2. Another Airgun Blog, Feb. 7, 2011. http://anotherairgunblog.blogspot.com/2011_02_01_archive.html.
Extended European Search Report for European Application No. 15851049.5, dated Jun. 19, 2018.

* cited by examiner

VARIABLE ECCENTRIC CAM RHEOMETER SYSTEM

CROSS REFERENCE TO RELATED APPLICATIONS

This application is a 371 U.S. National Stage of International Application No. PCT/US2015/054660 filed on Oct. 8, 2015, which claims the benefit of U.S. provisional application No. 62/063,611, filed on Oct. 14, 2014, both of which are incorporated by reference herein in their entirety.

BACKGROUND

1. Field

Aspects herein generally relate to rheometer systems for testing polymers, and more particularly to a variable eccentric cam rheometer system.

2. Discussion of Related Art

Polymers are often tested according to one of several ASTM methods, namely, ASTM D1646, D2084, D5289, and D6204. Instruments operating in accordance with ASTM D2084 and D5289 are known. For example, U.S. Pat. No. 3,681,980 illustrates the application of a fixed eccentric cam to facilitate oscillation of a rotor. This amplitude of oscillation is determined by the position of the pin on the eccentric. U.S. Pat. No. 4,794,788 also illustrates the use of an eccentric to facilitate an oscillatory motion. The amplitude of oscillation can be changed between tests by changing the position of the pin on the eccentric or by changing the eccentric to one with a different off-set.

ASTM D6204 describes the use of a variable frequency test, and also discloses the capability of performing a variable temperature test. ASTM D6601 describes the conditions for evaluating a specimen at more than one strain amplitude during a single test. This test may be used with the apparatus described in U.S. Pat. Nos. 4,794,788, 5,079,956 or 6,681,617.

Many of the apparatus described in these patents and used in the foregoing ASTM test methods are referred to as moving die rheometers. In typical moving die rheometers, two opposing co-axial dies compress a test specimen between them. One die is driven in an oscillatory manner, while the opposite die is free to rotate independently of the first die. A flex arm is connected to the one die, and this flex arm is driven back and forth to create the oscillatory movement of the one die. In these existing systems, a drive system may comprise an eccentric attached to the output of a motor. The eccentric is connected to a link arm which is further connected to a flex arm. The amplitude of movement of the one die is determined by the distance between the axis of rotation of the eccentric and the post of the eccentric. When one eccentric is removed and another is installed, or when the position of the post is altered, the phase may be shifted between the motor output and the one die because it is difficult to keep the phase constant. This process requires a recalibration of the rheometer every time a different amplitude is required. This recalibration is time-consuming, and increases the downtime of the rheometer.

SUMMARY OF INVENTION

In one aspect of the invention, an eccentric cam for use in an oscillating rheometer system is disclosed. The eccentric cam converts rotary motion into oscillatory motion of a die of the rheometer system. The eccentric cam includes a housing operatively connected to a rotating drive shaft which is structured to rotate the housing about a central axis of rotation, and a post slidably disposed in a channel in the housing, the post being connected to the die of the rheometer system by an arm, the post extending substantially parallel to the axis of rotation at a location which is spaced at a first desired distance from the axis of rotation. The eccentric cam further includes a first shim having a fixed dimension and being disposed in the cam housing to space the post at the desired first distance from the central axis of rotation, and at least one second shim having a different fixed dimension than the fixed dimension of the first shim, the first shim being removable from the housing for replacement with the second shim to change the location of the post to a second desired distance from the axis of rotation to change the amplitude of oscillation of the die. In one embodiment of this aspect, the eccentric cam further includes an elongated channel in the housing which passes through the central axis of rotation in a direction generally perpendicular to the axis of rotation, and a lock piece slidably disposed in the channel, in which the post extends from the lock piece. In another embodiment of this aspect, the first and second shims are inserted and removed from the channel through an opening in the housing in a direction that is generally perpendicular to a direction of elongation of the channel and generally perpendicular to the axis of rotation. In another embodiment, the eccentric cam further comprises a shaft that extends along the channel and through the lock piece, in which the shaft is threadably coupled to a face of the housing. In another embodiment of this aspect, the first or second shim is disposed between the lock piece and the face of the housing, and a torque may be applied to the shaft to thread the shaft into the face to urge the lock piece against the first or second shim and to urge the first or second shim against the face. In another embodiment of this aspect, the lock piece includes two blocks, a first block to which the post is attached and a second block, and wherein a head of the shaft bears against the second block, and the second block bears against the first block to urge the first block against the shim. In another embodiment of this aspect, the face of the housing is disposed at a location spaced from the axis of rotation on a side of the axis if rotation opposite that of the post. In yet another embodiment of this aspect, the first and second blocks bear against each other along substantially parallel surfaces, and wherein the substantially parallel surfaces form an acute angle with respect to the shaft.

Another aspect of this invention includes a method for changing the amplitude of oscillation of a moving die rheometer in which the rheometer comprises a housing operatively connected to a rotating drive shaft to rotate therewith about a central axis of rotation and a post slidably disposed on the housing, the post being connected to one end of an arm, and the other end of the arm being connected to a moving die in the rheometer to impart oscillatory motion thereto, the post being spaced from the central axis and generally parallel thereto. The method of this aspect includes selecting a first shim of a first known dimension to space the post a first distance from the central axis of rotation to impart a first amplitude of oscillation to the die, and changing the first known distance to a second known distance from the central axis of rotation by removing the first shim and replacing it with a second shim having a second known dimension to impart a second amplitude of oscillation to the die.

BRIEF DESCRIPTION OF DRAWINGS

The accompanying drawings are not intended to be drawn to scale. In the drawings, each identical or nearly-identical component that is illustrated in various figures is represented by a like numeral. For purposes of clarity, not every component may be labeled in every drawing. Various embodiments of the invention will now be described by way of example with reference to the accompanying drawings, in which.

DETAILED DESCRIPTION

Figure 1:
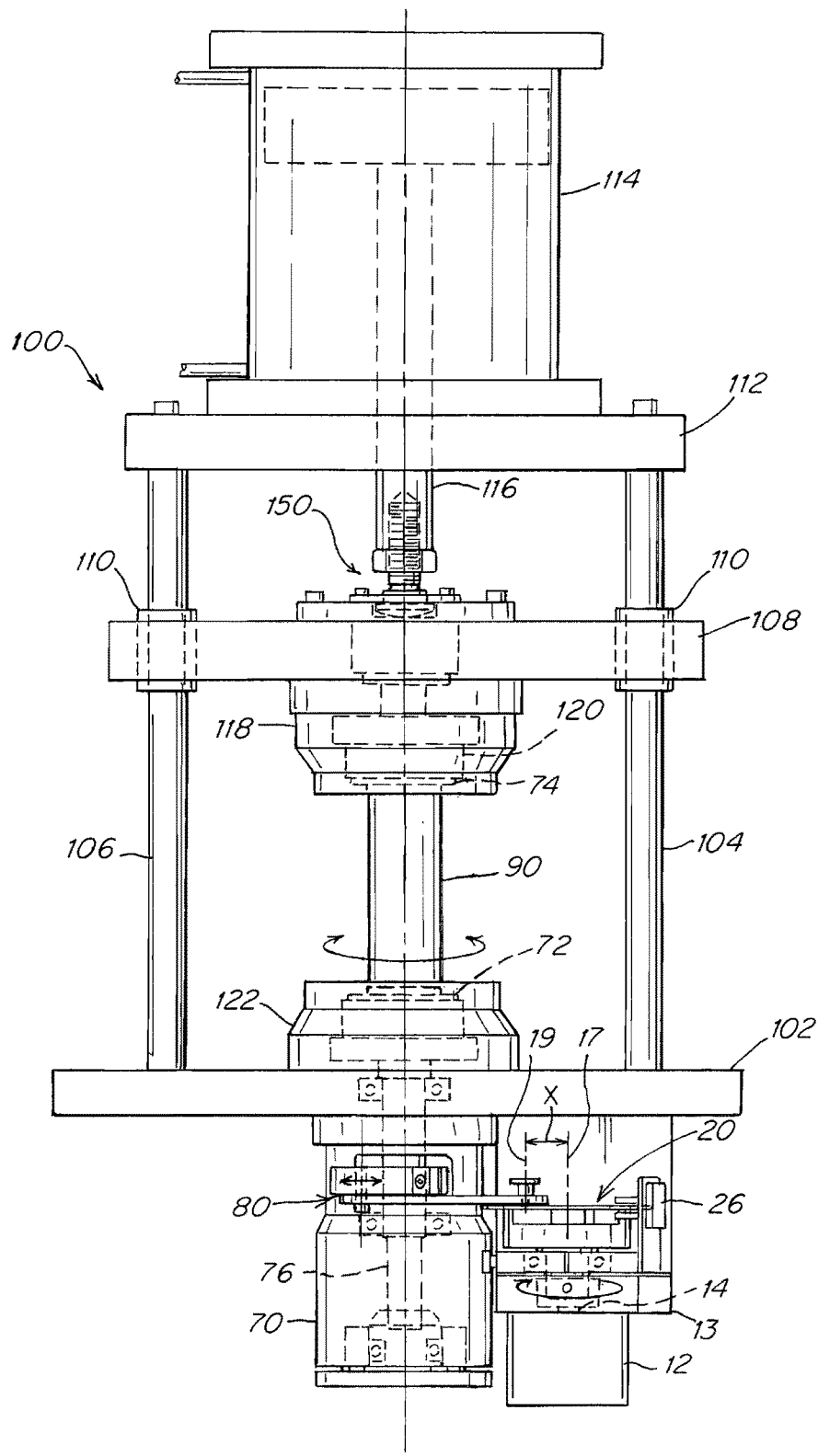
FIG. 1 is a front schematic view of a rheometer in accordance with one aspect of the invention.
Figure 2:
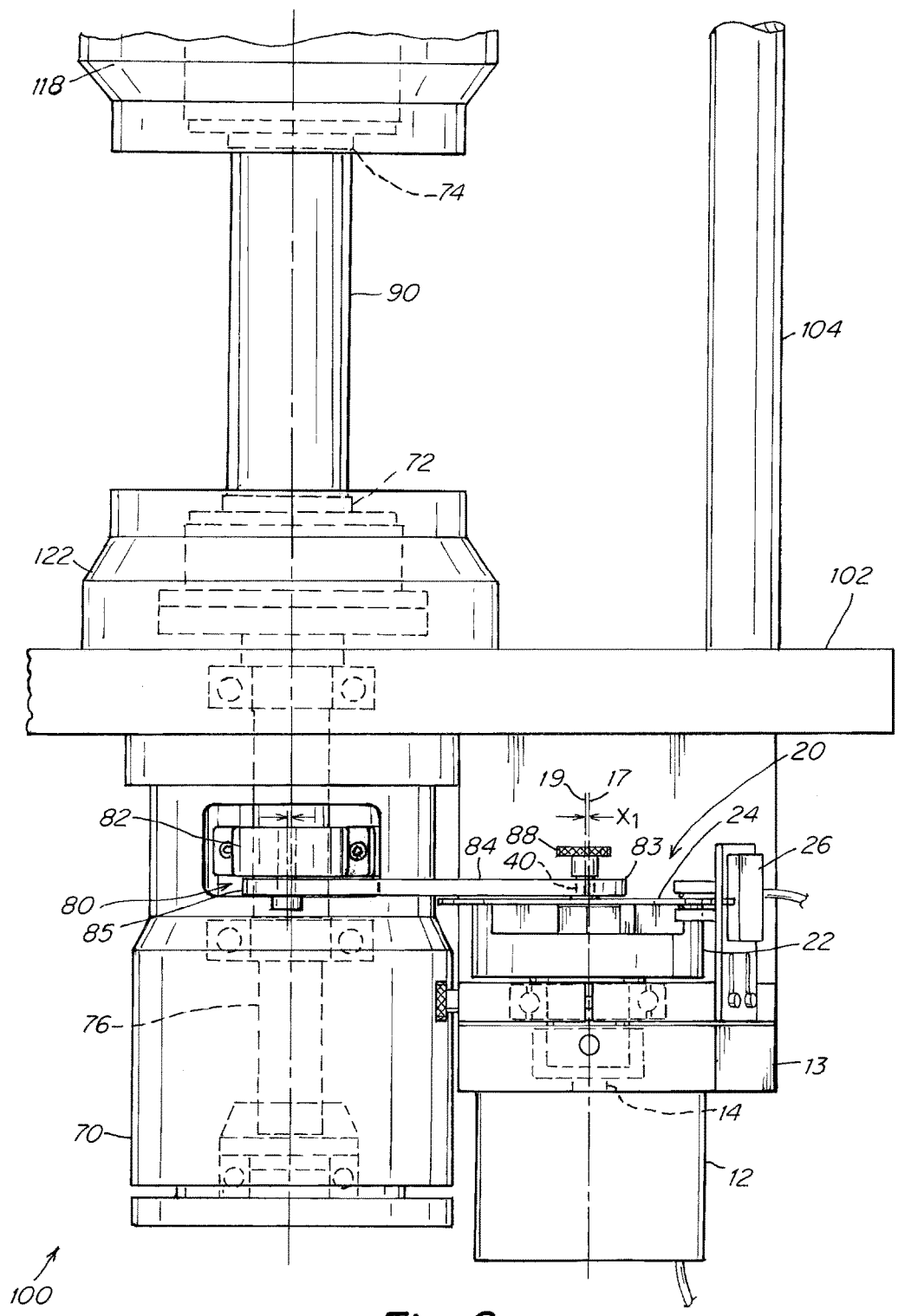
FIG. 2 is a partial, front schematic view of the rheometer of FIG. 1.
Figure 3:
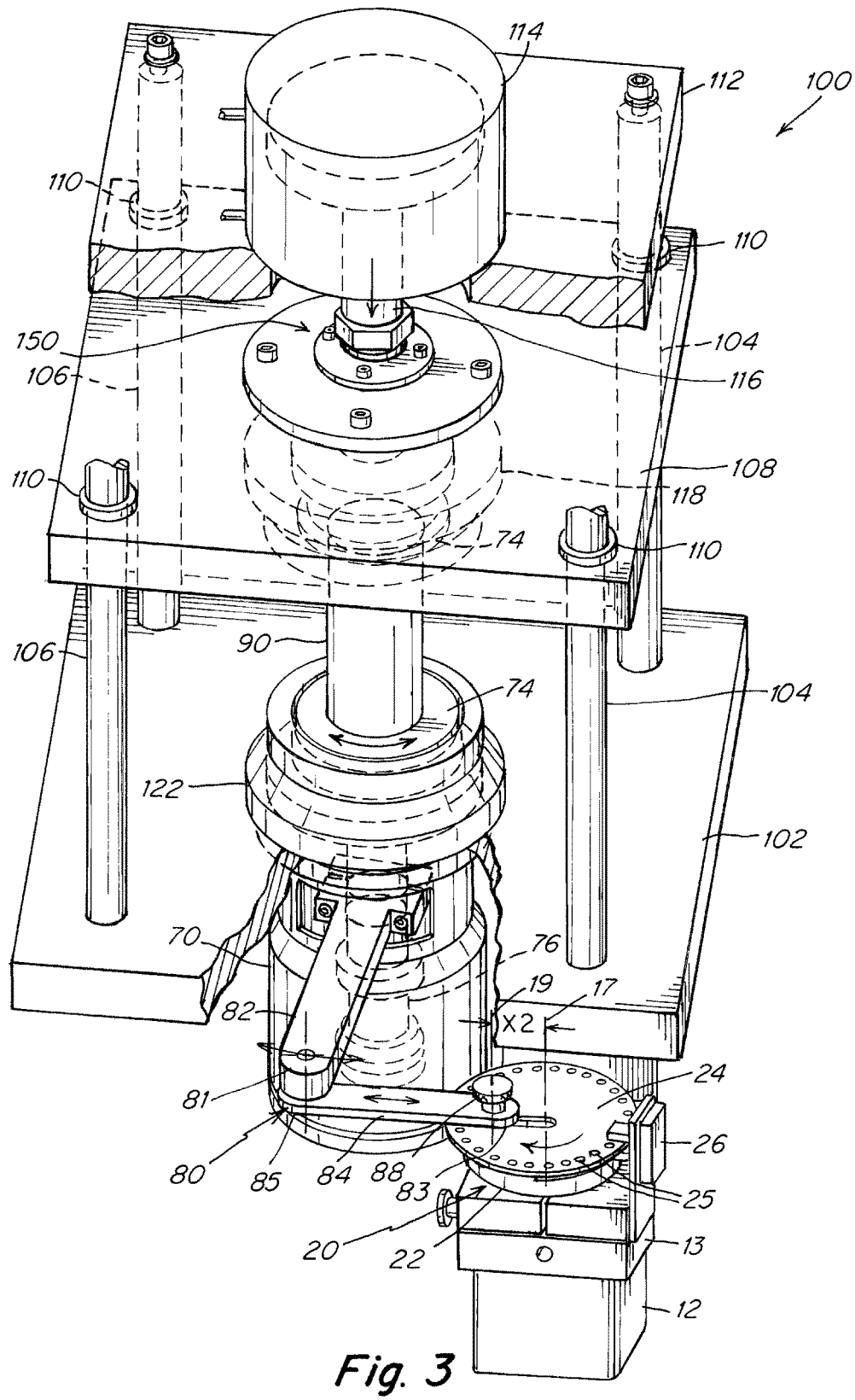
FIG. 3 is a perspective, schematic view of the rheometer of FIG. 1.
Figure 4:
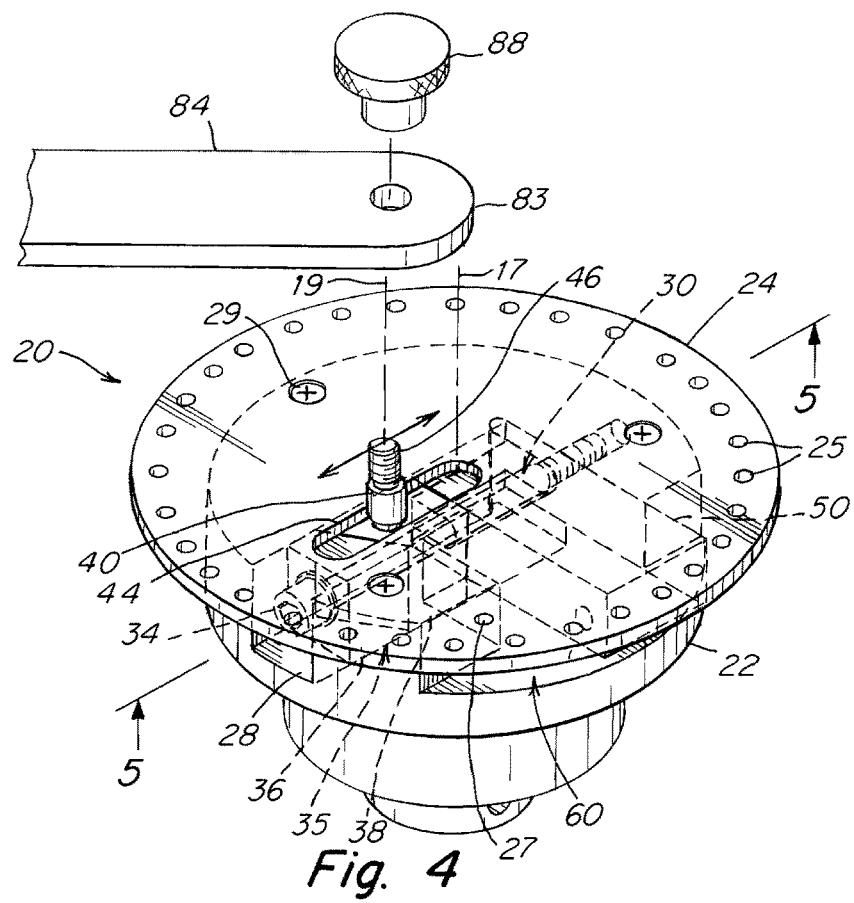
FIG. 4 is an exploded, perspective view of the variable eccentric mechanism of the rheometer of FIG. 1.
Figure 5:
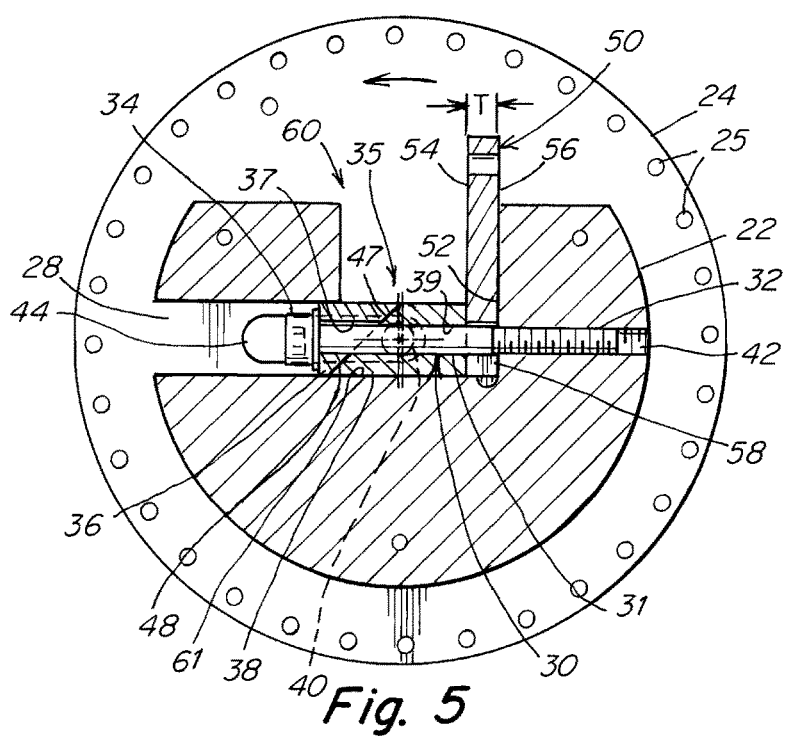
FIG. 5 is a cross-sectional plan view of the mechanism of FIG. 4 taken along a line 5-5 of FIG. 4.
Figure 6:
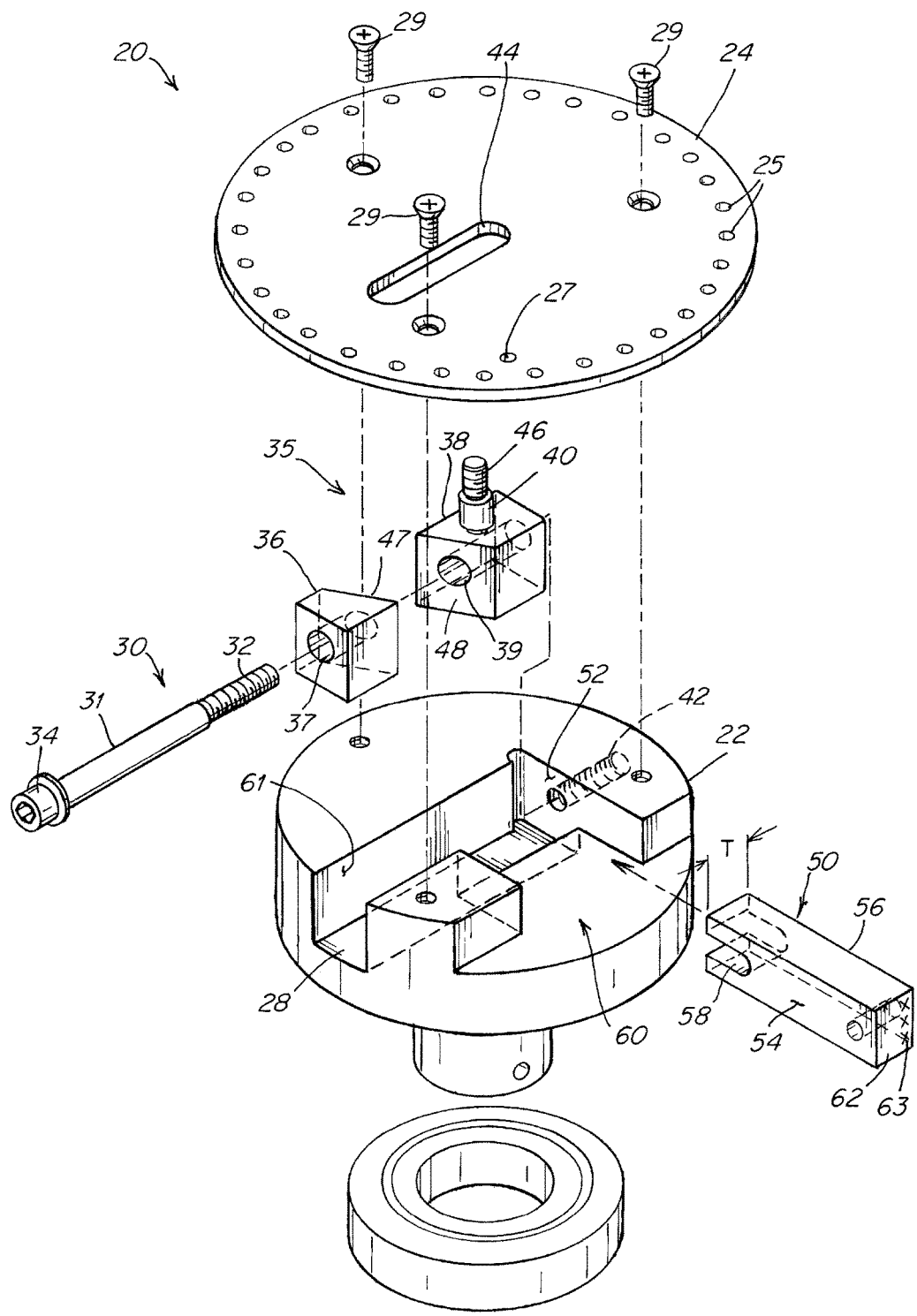
FIG. 6 is an exploded, perspective view of the mechanism of FIG. 5.

This invention relates to an improved, variable eccentric rheometer system for testing polymers. In one aspect, a variable eccentric is provided which permits the amplitude of oscillation of the die to be changed without the need to recalibrate. In this aspect of the invention, shims of different widths may be inserted into the variable eccentric to position the post at pre-defined locations with respect to the center of rotation of the variable eccentric assembly. The shims may be inserted and removed through the use of a threaded shaft which bears on angled blocks of a lock piece which holds the shim in position. The lock piece is carefully calibrated so that a precise location of the post is assured.

With reference now to the drawings, and more particularly to FIGS. 1-4 thereof, one embodiment of a moving die rheometer (MDR) will now be described. MDR 100 typically includes a main plate 102 and posts 104 and 106 mounted to and extending upwardly from main plate 102. A cross-head 108 rides upwardly and downwardly along posts 104 and 106 on bearings 110. A cylinder mounting plate 112 sits on top of posts 104 and 106. Mounted on top of the cylinder mounting plate is an air or gas cylinder 114. Instead of an air cylinder, any other known drive apparatus could be used such as an electric or gasoline motor or a hydraulic system. A cylinder shaft 116 extends downwardly from air cylinder 114 through cylinder mounting plate 112. The cylinder shaft 116 is mounted to cross-head 108 by a coupling system 150, so as to allow air cylinder 114 to drive cross-head 108 upwardly and downwardly along posts 104 and 106. Suspended from cross-head 108 is an upper housing 118 which includes a torque transducer 120. Disposed on a lower end of upper housing 118 is an upper die 74.

Mounted onto main plate 102 is a lower housing 122, and disposed below lower housing 122 and mounted to main plate 102 is a central stack housing 70. Disposed on the upper end of lower housing 122 is lower sample die 72. Mounted on main plate 102 and disposed adjacent central stack housing 70 is a drive motor 12 which is coupled to an eccentric cam 20. Drive motor 12 rotates a drive shaft 14. Motor 12 is attached to motor mount 13. Drive shaft 14 is rigidly affixed to eccentric cam 20 so that rotation of drive shaft 14 is directly transferred to eccentric cam 20. Eccentric cam 20 has a central axis of rotation 17 passing through the center thereof, and through the center of drive shaft 14. A die shaft 76 passes through the center of central stack housing 70 and is rigidly affixed to sample die 72. Die shaft 76 in turn is coupled to eccentric cam 20, by link assembly 80, which may include link arm 84 and flex arm 82. Link arm 84 is coupled at one end 83 to a post 40 of eccentric cam 20, and at the other end 85 to an end 81 of flex arm 82. In one embodiment, end 83 is coupled to post 40 through the use of a knurled thumb nut 88 which is screwed onto threads 46 on post 40. Flex arm 82 in turn is coupled at the opposite end to die shaft 76. Rotation of drive shaft 14 by motor 12 causes rotation of eccentric cam 20, such that end 83 of link arm 84 rotates about the central axis of rotation 19 of post 40 of eccentric cam 20 to cause flex arm 82 to move in an oscillatory motion, which motion is then transferred by link assembly 80 through die shaft 76 to sample die 72.

During testing of a polymer specimen 90, specimen 90 is positioned on lower die 72. When air cylinder 114 is activated, cylinder shaft 116 moves cross-head 108 downwardly to urge upper housing 118 toward lower housing 122. Polymer specimen 90 is then captured between lower die 72 and upper die 74. Oscillatory motion is produced on lower sample die 72. During testing, heat may be applied to the specimen 90 in a conventional manner. Torque transducer 120 measures the reaction torque that is the result of the resistance of the polymer specimen 90 to the oscillatory motion. A test method that may be used with MDR 100 includes ASTM D5289. When employing MDR 100, a measurement may first be made at one amplitude of oscillation, and after a change in the amplitude of oscillation, another measurement would be made, and so forth.

In one aspect of the invention, an embodiment of eccentric cam 20 will now be described with respect to FIGS. 4-7. Eccentric cam 20 may include a cover 24 and a base 22. In one embodiment of the invention, cover 24 is attached to base 22 using screws 29. Base 22 may be in the shape of a cylinder and may include known features to allow attachment of base 22 to drive shaft 14. Cover 24 may include indicia, such as a ring of holes 25 around the perimeter of cover 24, which are sensed by a disk encoder 26. Cover 24 in conjunction with disk encoder 26 permit measurement of the speed of rotation of eccentric cam 20 and the position of eccentric cam 20, in a manner known to one of skill in the art. The ring of holes 25 may include 32 equally spaced holes. There may also be one other zero hole 27 spaced radially inwardly of the ring of holes 25. The disk encoder 26 reads hole 27 to determine the zero strain angle point. Knowing these points allows determination of the position of the eccentric cam 20 at every hole 25. Also, these readings allow a controller (not shown) to calculate the reaction torque generated by torque transducer 20 as the physical properties of polymer specimen 90 change during testing.

Disposed within base 22 of eccentric cam 20 is a channel 28 which extends radially outwardly from a location closely adjacent but offset from the axis of rotation 17, through the axis of rotation 17 and to an opposite side of base 22. Passing through channel 28 is a shaft 30 which includes screw threads 32 on one end, a head 34 on the other end, and an unthreaded portion 31 between. Head 34 is configured to be accessible within channel 28 from outside cam 20. Head 34 typically is configured to be engaged by a device for rotation of shaft 30 in a clockwise or counter-clockwise direction, such as a screwdriver, an Allen wrench or the like. Threads 32 are configured to engage a mating, threaded channel 42 disposed in base 22, so that shaft 30 may be screwed into and out of channel 42 by application of rotational torque to head 34.

Disposed between head 34 and threads 32 is a lock piece 35, which may include two blocks 36 and 38. Blocks 36 and 38 may include respective channels 37 and 39 through which portion 31 of shaft 30 may pass. Typically, but not necessarily, there are no threads in channels 37 and 39. Positioned on block 38 is post 40 which extends upwardly through a slot 44 in cover 24. Post 40, in turn, is coupled to end 83 of link arm 84, as described. In one embodiment, post 40 may be coupled to block 38 by means of screw threads 46 with a lock washer. Both of blocks 36 and 38 are permitted to travel along channel 28 in a direction parallel to shaft 30. In one embodiment, surface 47 of block 36 may engage block 38 along a parallel surface 48. Parallel surfaces 47 and 48 typically are not oriented perpendicular to shaft 30, but form an acute angle with respect to shaft 30. This angle may be about 45°, although other angles may be used. Blocks 36 and 38 preferably are formed of a hardened material that does not deform to any significant degree when subjected to pressure applied when shaft 30 is tightly screwed into place. One example of such a material is hardened steel. This configuration permits the precise placement of post 40 at a desired spacing from axis 17 within channel 28, when block 38 containing post 40 is locked into place in a specific, desired, location within channel 28. The positon of post 46, the distance between axis 17 and axis 19 and thus the amount of eccentric motion provided to assembly 80 is carefully controlled. In one embodiment, the distance X may range from about $X_1$ shown in FIG. 2 to about $X_2$ shown in FIG. 3. Distance $X_1$ may be about 0.6161 mm (0.0243 in) and distance $X_2$ may be about 22.0269 mm (0.8672 in). Greater or lower values for $X_2$ and $X_1$ respectively may be used. The $X_1$ value of 0.6161 mm corresponds to a strain angle of 0.2 degrees, while the $X_2$ value of 22.0268 mm corresponds to a strain angle of 7.17 degrees. The strain angle is the angle through which lower sample die 72 oscillates or moves back and forth. In one embodiment, strain angles of 0.2 degrees, 0.5 degrees, 1.0 degrees, 3.0 degrees and 7.17 degrees may be used.

In one aspect, the positioning of block 38, and thus post 40, is achieved through the use of one or more shims 50. Each shim 50 has a precisely known thickness T (FIG. 6) between front and back faces 54 and 56 which determines the distance between block 38 and surface 52. This distance determines the position of post 40 in slot 44 and the distance between axes 17 and 19. Each shim 50 includes a slot 58 through which shaft 30 may pass. Each shim 50 is inserted and retracted through an opening 60 disposed between cover 24 and base 22, in a direction generally perpendicular to channel 28. Each shim 50 may have any suitable shape, although in one embodiment, each shim 50 has a rectangular shape with a square or rectangular cross-section. Shims 50 are formed of a hardened material such as hardened steel. A shim 50 may be inserted or removed by first rotating shaft 30 in one direction, such as a counterclockwise direction, to unscrew threads 32 from threaded channel 42 a sufficient distance to permit one shim 50 to be removed, and a second shim 50 of a different thickness T to be inserted. Once a shim 50 has been inserted, a torque in an opposite direction, such as a clockwise direction, is applied to shaft 30 via head 34 to screw threads 32 into channel 42 to drive block 36 against block 38 along respective faces 47 and 48 until the blocks are driven tightly together, and until shim 50 is tightly captured between block 38 and face 52. The angled surfaces 47 and 48 not only force block 38 containing post 40 against face 54 of shim 50, but also force block 38 lightly against face 61 of channel 28 when shaft 30 is screwed into channel 42. At this point, post 40 has a precisely known positon within slot 44 and the distance between axes 17 and 19 produces the desired eccentric motion. Each shim 50 may have indicia 63 on an outer face 62 to provide a user with an identification showing the thickness T of that particular shim. The thicker the shim 50, the greater is the distance between axes 17 and 19, the greater is the eccentricity provided by cam 20, and in turn, the greater is the amplitude of oscillation of the sample die 72.

Operation of MDR100 of this application will now be described. Actuation of motor 12 produces rotary motion about drive shaft 14 which in turn rotates cam 20 about its axis 17. Encoder 26 measures the speed of rotation of cam 20 and provides data to a controller (not shown). In most operations, axis 19 of post 40 is spaced a predetermined distance X from the axis 17. This distance is determined by, and typically corresponds to, thickness T of shim 50. Cam 20 produces oscillatory motion in link arm 84 which transfers the oscillatory motion to flex arm 82. This oscillatory motion is then transferred to die shaft 76 which in turn imparts oscillatory motion to sample die 72.

Figure 7:
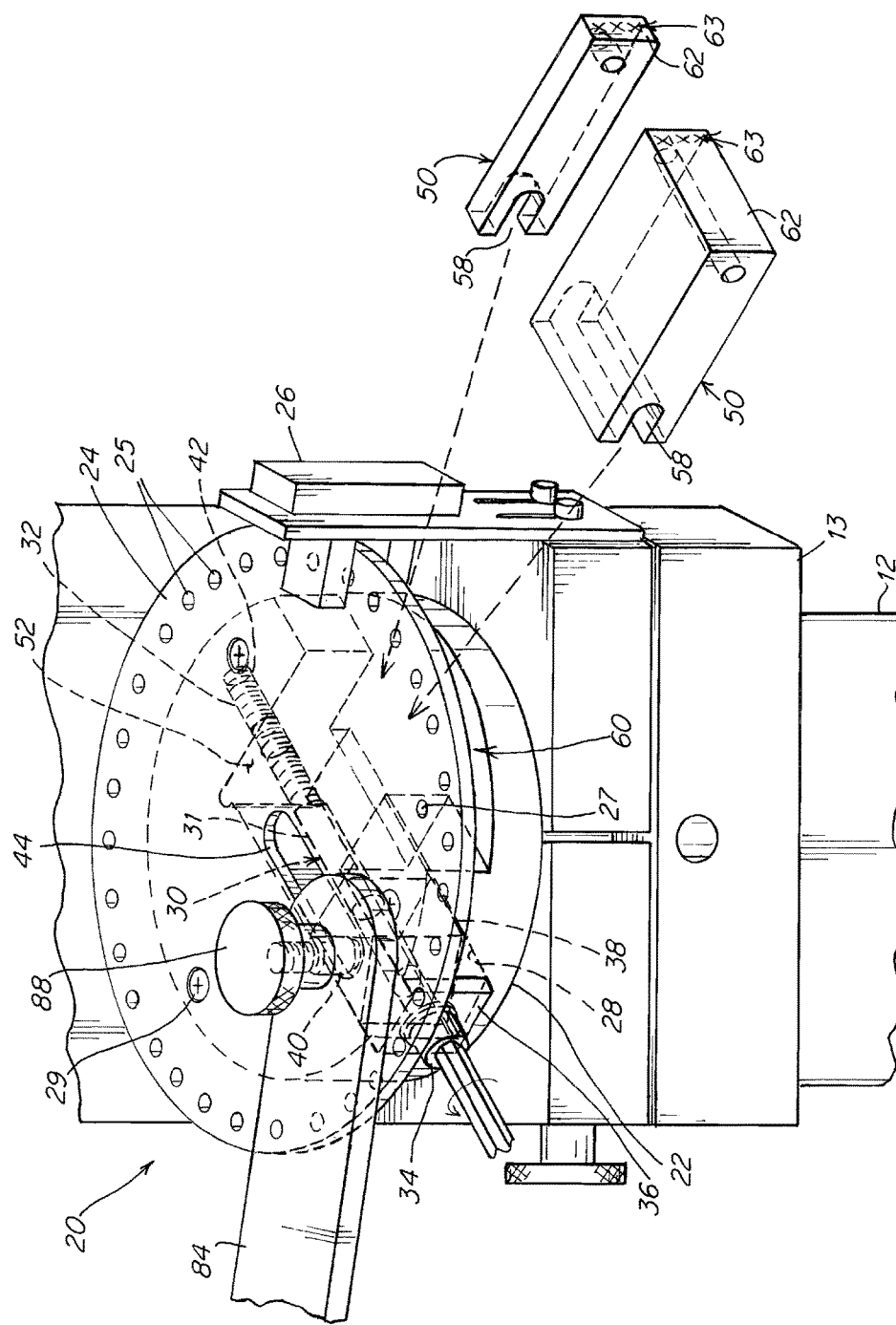
FIG. 7 is a perspective view showing the process of changing shims in the mechanism of FIG. 5.

When it is desired to change the amplitude of oscillation, the location of post 40 with respect to the axis of rotation 17 of cam 20 is changed. If it is desired to create a larger amplitude of oscillation, axis 19 of post 40 is moved to a greater distance from the axis of rotation 17 of cam 20. If it is desired to reduce the amplitude of oscillation, axis 19 of post 40 is moved to a distance closer to the axis of rotation 17 of cam 20. First, shaft 30 is partially unscrewed from threaded channel 42 by applying a rotational torque to head 34 in a first, typically counterclockwise, direction. Once shaft 30 has been withdrawn a specified distance through rotation, the shim 50, which is already present in cam 20, is released and may be removed by sliding it out through opening 60 in a direction substantially perpendicular to shaft 30, as shaft 30 passes through slot 58 of shim 50. As seen in FIG. 7, a new shim 50 may be selected from an existing collection of shims 50 of various thicknesses T based upon the indicia 63 on face 62. Either the largest shim 50 shown on the left in FIG. 7 or any shim 50 down to the smallest shim 50 shown on the right in FIG. 7 may be selected. Each thickness T is associated with a certain amplitude of oscillation, and a certain strain angle. The desired shim 50 is slid into cam 20 through opening 60 such that shaft 30 passes through slot 58. Two or more shims could also be used in tandem if desired. Once shim 50 is pushed into cam 20 as far as permitted through opening 60, head 34 is rotated in the opposite direction, typically a clockwise direction, to screw shaft 30 into threaded channel 42. This rotation forces block 36 against block 38 along respective surfaces 47 and 48 until surfaces 47 and 48 are tightly pressed against one another, and until block 38 is pressed tightly against face 54 of shim 50 and face 61. A predetermined amount of torque is applied until the shim is tightly held between block 38 and face 52. At this point, rheometer 100 may again be activated to produce the desired oscillatory movement.

The insertion of a new shim 50 into eccentric cam 20 may cause a slight change in phase angle between the motor output and lower sample die 72. The phase angle is the result of machine error. Hole 27 is intended to represent the position of zero strain when it is read by encoder 26. However, each machine typically does not actually generate zero strain at that point. This error is known as the phase angle. Each size shim is typically associated with a different phase angle. However, the phase angle for each size shim is known because post 40 is in exactly the same position each time a particular shim 50 is used. A calibration for each size shim 50 is saved in the controller software. Thus the calibration required for each change of shim 50 is done automatically and instantaneously in the software. As a result, there is no downtime required for recalibration.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An eccentric cam for use in an oscillating rheometer system wherein the eccentric cam converts rotary motion into oscillatory motion of a die of the rheometer system, the eccentric cam comprising:
    a housing operatively connected to a rotating drive shaft which is structured to rotate the housing about a central axis of rotation;
    a post slidably disposed in a channel in the housing, the post being connected to the die of the rheometer system by an arm, the post extending parallel to the axis of rotation at a location which is spaced at a first desired distance from the axis of rotation;
    a first shim having a fixed dimension and being disposed in the cam housing to space the post at the desired first distance from the central axis of rotation; and
    at least one second shim, having a different fixed dimension than the fixed dimension of the first shim, the first shim being removable from the housing for replacement with the second shim to change the location of the post to a second desired distance from the axis of rotation to change the amplitude of oscillation of the die.

2. The eccentric cam of claim 1 further comprising:
    an elongated channel in the housing, the channel passing through the central axis of rotation in a direction perpendicular to the axis of rotation; and
    a lock piece slidably disposed in the channel, the lock piece having the post extending therefrom.

3. The eccentric cam of claim 2 wherein the first and second shims are inserted and removed from the channel through an opening in the housing in a direction that is perpendicular to a direction of elongation of the channel and perpendicular to the axis of rotation.

4. The eccentric cam of claim 2 further comprising a shaft that extends along the channel and through the lock piece, the shaft being threadably coupled to a face of the housing.

5. The eccentric cam of claim 4 wherein the first or second shim is disposed between the lock piece and the face of the housing and wherein a torque is applied to the shaft to thread the shaft into the face to urge the lock piece against the first or second shim and to urge the first or second shim against the face.

6. The eccentric cam of claim 5 wherein the lockpiece comprises two blocks, a first block to which the post is attached and a second block, and wherein a head of the shaft bears against the second block and the second block bears against the first block to urge the first block against the shim.

7. The eccentric cam of claim 5 wherein the face of the housing is disposed at a location spaced from the axis of rotation on a side of the axis of rotation opposite that of the post.

8. The eccentric cam of claim 6 wherein the first and second blocks bear against each other along parallel surfaces and wherein the parallel surfaces form an acute angle with respect to the shaft.

9. A method for changing the amplitude of oscillation of a moving die rheometer, in which the rheometer comprises:
    a housing operatively connected to a rotating drive shaft to rotate therewith about a central axis of rotation; and
    a post slidably disposed on the housing, the post being connected to one end of an arm, the other end of the arm being connected to a moving die in the rheometer, the post being spaced from the central axis and parallel thereto;
the method comprising:
    selecting a first shim of a first known dimension to space the post a first known distance from the central axis of rotation to impart a first amplitude of oscillation to the die; and
    changing the first known distance to a second known distance from the central axis of rotation by removing the first shim and replacing it with a second shim having a second known dimension to impart a second amplitude of oscillation to the die.

* * * * *